(12) United States Patent
Murakami et al.

(10) Patent No.: US 7,276,080 B2
(45) Date of Patent: Oct. 2, 2007

(54) INTRAOCULAR LENS

(75) Inventors: Naho Murakami, Hoi-gun (JP);
Yoshihiro Nakahata, Gamagori (JP);
Tsutomu Sunada, Toyohashi (JP)

(73) Assignee: Nidek Co. Ltd. (JP)

( * ) Notice: Subject to any disclaimer, the term of this patent is extended or adjusted under 35 U.S.C. 154(b) by 275 days.

(21) Appl. No.: 10/900,589

(22) Filed: Jul. 28, 2004

(65) Prior Publication Data
US 2005/0027355 A1    Feb. 3, 2005

(30) Foreign Application Priority Data
Jul. 31, 2003    (JP)    ............................... 2003-283565

(51) Int. Cl.
*A61F 2/16*    (2006.01)
(52) U.S. Cl. ...................... 623/6.3; 623/6.31
(58) Field of Classification Search ............. 623/6.11, 623/6.17, 6.23–6.36, 6.6, 6.62
See application file for complete search history.

(56) References Cited
U.S. PATENT DOCUMENTS
4,759,761 A    7/1988    Portnoy 6,913,620 B2 *    7/2005    Lipshitz .................... 623/6.32

FOREIGN PATENT DOCUMENTS
JP    62-221345    9/1987

\* cited by examiner

*Primary Examiner*—Corrine McDermott
*Assistant Examiner*—William H Matthews
(74) *Attorney, Agent, or Firm*—Rader Fishman & Grauer PLLC; Ronald P. Kananen

(57) ABSTRACT

An intraocular lens for amblyopia designed in consideration of normalizing vision as well as magnifying vision, is provided with an optical part having predetermined refractive power, which includes front and rear side refractive surfaces, a supporting part for supporting the optical part within the eye, a first reflecting part formed at a rear surface side of the optical part for reflecting an incident light bundle, which has passed through the front surface of the optical part, toward the front surface, and a second reflecting part formed at a front surface side of the optical part for reflecting the incident light bundle, which has been reflected by the first one, toward the rear surface, wherein the first and second reflecting parts form a reflecting telescopic system which forms a magnified image on a retina, and at least one of them has a property of transmitting a part of the light bundle.

4 Claims, 2 Drawing Sheets

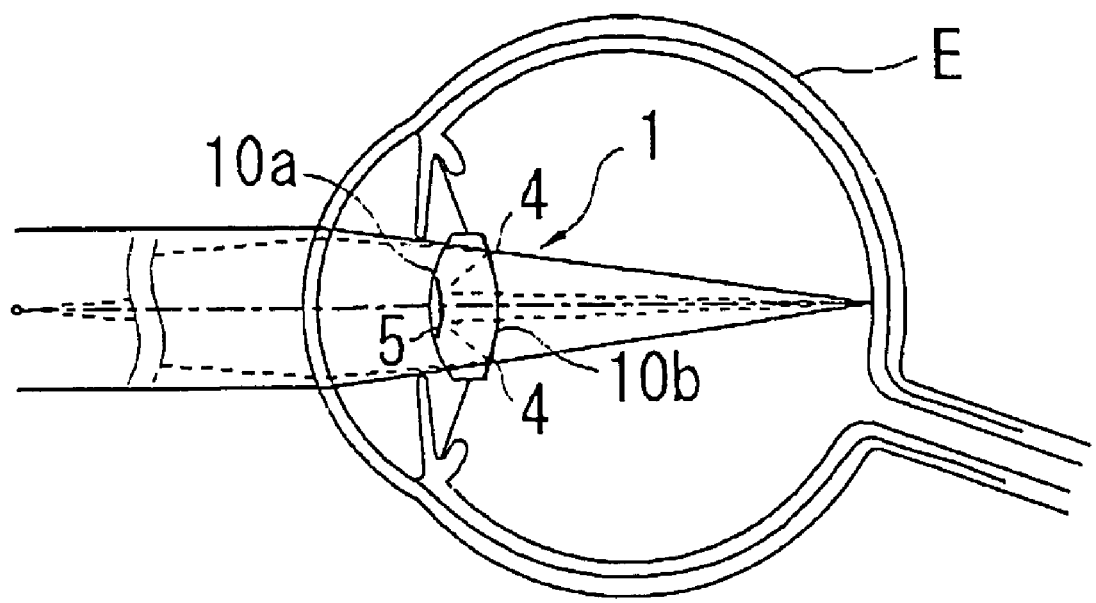
FIG. 3
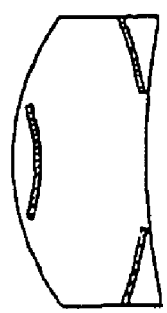 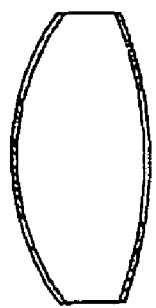 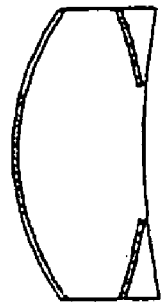
FIG. 4A    FIG. 4B    FIG. 4C

INTRAOCULAR LENS

BACKGROUND OF THE INVENTION

1. Field of the Invention

The present invention relates to an intraocular lens, more specifically relates to an intraocular lens for amblyopia.

2. Description of Related Art

There is an intraocular lens for amblyopia provided with a telescopic (magnifying) function. As the intraocular lens, for example, such an intraocular lens is proposed that incorporates reflectors producing an effect of a folded telescope with a long focal length (refer to U.S. Pat. No. 4,759,761 corresponding to Japanese Patent Application Unexamined Publication No. Sho62-221345).

However, this proposed intraocular lens is designed such that only an object located at a predetermined short (near) distance in front may be seen under magnification (i.e., such that an image of the object located at the predetermined short distance in front may be formed (focused) on a retina as a magnified image) without considering how to be seen with a normal phakic eye (normalizing vision). Therefore, an image of an object located at an infinite distance (a long (far) distance) in front is not formed (not focused) on the retina, so that it often imposes inconvenience to a wearer.

SUMMARY OF THE INVENTION

The present invention has been made in view of the above circumstances and has an object to overcome the above problems and to provide an intraocular lens for amblyopia designed in consideration of normalizing vision as well as magnifying vision.

To achieve the objects and in accordance with the purpose of the present invention, an intraocular lens arranged inside an eye is provided with an optical part having predetermined refractive power which includes a front side refractive surface and a rear side refractive surface, a supporting part for supporting the optical part within the eye, a first reflecting part formed at a rear surface side of the optical part for reflecting an incident light bundle, which has passed through the front surface of the optical part, toward the front surface, and a second reflecting part formed at a front surface side of the optical part for reflecting the incident light bundle, which has been reflected by the first reflecting part, toward the rear surface, and wherein the first reflecting part and the second reflecting part form a reflecting telescopic system which forms a magnified image on a retina of the eye, and at least one of the first reflecting part and the second reflecting part has a property of transmitting a part of the incident light bundle.

In another aspect of the present invention, an intraocular lens arranged inside an eye is provided with an optical part including a front side refractive surface and a rear side refractive surface, a supporting part for supporting the optical part within the eye, and an image forming optical system provided for the optical part for forming an image under approximately the same magnification as an image seen with a phakic eye as well as forming a magnified image on a retina of the eye.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 3 is a view showing image formation of a light bundle when the intraocular lens is arranged inside an eye;

FIGS. 4A to 4C are views showing modified embodiments of the intraocular lens consistent with the present invention.

DETAILED DESCRIPTION OF THE PREFERRED EMBODIMENTS

Figure 1:
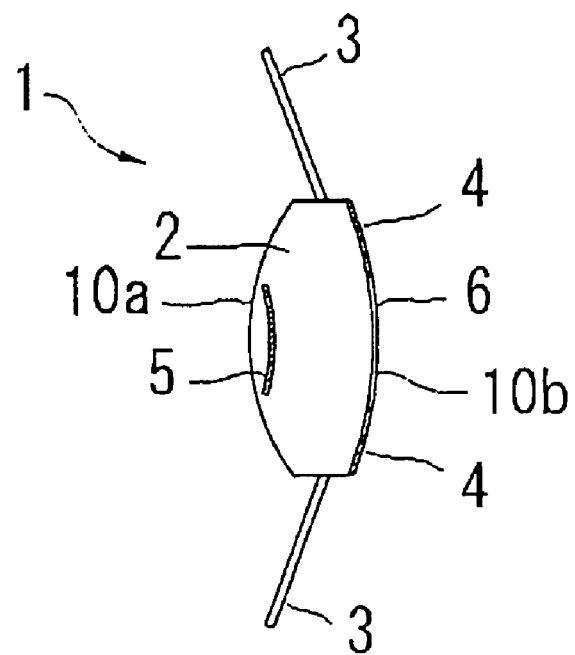
FIG. 1 shows a schematic configuration of an intraocular lens for amblyopia consistent with the preferred embodiment.

A detailed description of one preferred embodiment of an intraocular lens consistent with the present invention is provided below with reference to the accompanying drawings. FIG. 1 shows a schematic configuration of an intraocular lens for amblyopia consistent with the preferred embodiment of the present invention. Besides, a front side refers to a corneal side of the intraocular lens arranged inside an eye, and a rear side refers to a fundus side thereof. The intraocular lens 1 includes an optical part 2 which has predetermined refractive power, and supporting parts 3 which support and fix the optical part 2 within the eye. The intraocular lens 1 consistent with the preferred embodiment is a three-piece-type one which is prepared in such a manner that the optical part 2 and the supporting parts 3 are separately formed and then joined.

The optical part 2 is formed of a material which has been conventionally used for an optical part of an intraocular lens. For example, it is formed of a hard material such as PMMA (polymethyl methacrylate), a single soft material such as silicone or HEMA (hydroxyethyl methacrylate), or a complex soft material such as a combination of acrylic ester and methacrylate ester. Besides, an ultraviolet absorber, a coloring agent and the like may be added to these materials accordingly. Further, the supporting parts 3 are also formed of a material which has been conventionally used for a supporting part of an intraocular lens. For example, it is formed of PMMA, polypropylene, polyimide or the like.

As shown in FIG. 1, the optical part 2 has a biconvex shape, where a front side refractive surface (hereinafter referred to as a front surface) 10*a* and a rear side refractive surface (hereinafter referred to as a rear surface) 10*b* have predetermined curvature (determined by the refractive power which the optical part 2 is to have) respectively. This is a shape of a general intraocular lens (for a cataract treatment) which is arranged inside the eye to substitute for a crystalline lens. Further, at the rear surface 10*b* side of the optical part 2, a reflecting part (reflector) 4 having a half-mirror function is formed, which transmits a part of an incident light bundle that has passed through the front surface 10*a* and reflects the other part thereof toward the front surface 10*a*. Furthermore, at the front surface 10*a* side of the optical part 2, a reflecting part (reflector) 5 having the half-mirror function is formed, which transmits a part of the incident light bundle that has been reflected by the reflecting part 4 and reflects the other part thereof toward the rear surface 10*b*. Incidentally, the reflecting part 4 is formed to be approximately ring-shaped on a peripheral part at the rear surface 10*b* side, and the reflecting part 5 is formed to be approximately circular in a central part at the front surface 10*a* side.

As described above, the intraocular lens 1 (the optical part 2) has refractive power of a general intraocular lens (an intraocular lens which substitutes for the crystalline lens), and further has a reflecting telescopic system (shown in the embodiment of FIG. 1 is a Cassegrainian reflecting telescopic system) which is formed by the reflecting parts 4 and 5. Then, a configuration described above allows the light bundle, which has passed through the optical part 2, to form an image on the retina, so that an image under normal magnification (an image under approximately the same magnification as an image seen with a phakic eye) may be obtained (normalizing vision), and further the configuration allows the light bundle, which has been reflected by the reflecting parts 4 and 5, to form an image on the retina, so that an image under high magnification may be obtained (magnifying vision).

Besides, reference numeral 6 is a coating layer for preventing the reflecting part 4 from directly contacting a living body as well as from falling off.

Figure 2:
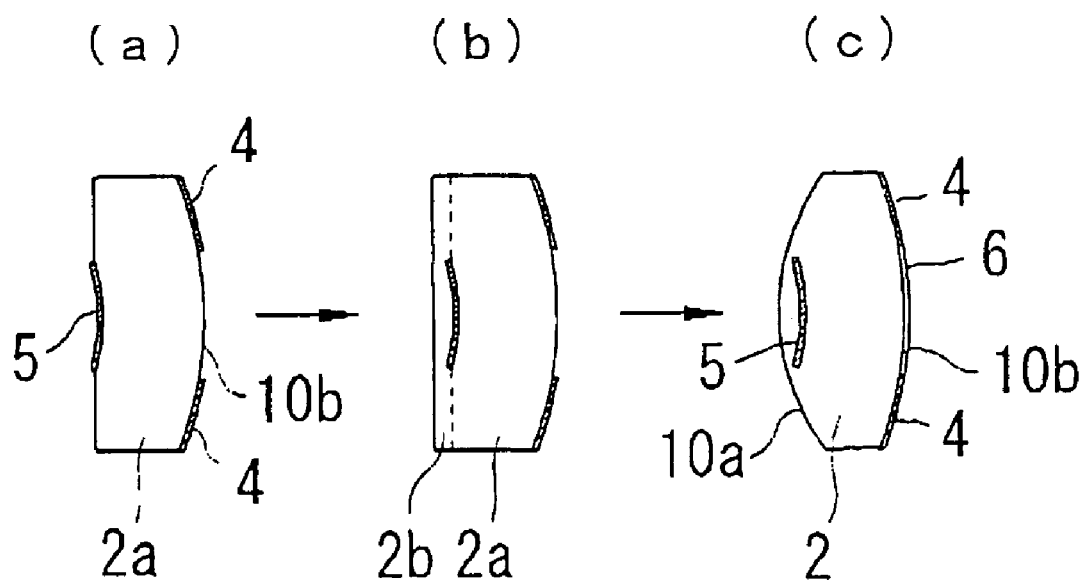
FIG. 2 is a view showing a process for manufacturing the present intraocular lens.

Next, a process for manufacturing the above-described intraocular lens 1 is explained based on FIG. 2. First, a flat plate 2a is formed by polymerizing and hardening the above-described material for the optical part 2. The rear surface 10b having the predetermined curvature is formed on a rear surface of the flat plate 2a by cutting thereof, and a concave part for forming the reflecting part 5 is formed in a predetermined area in a central part of a front surface of the flat plate 2a by cutting thereof (see the step (a) in FIG. 2). Then, a half-mirror coating is applied to this flat plate 2a to form the reflecting parts 4 and 5; after masking a part of the flat plate 2a where is not to be coated, the reflecting parts 4 and 5 are formed by depositing a material for a half mirror such as chrome (Cr) on the flat plate 2a by means of vacuum deposition or the like (see the step (a) in FIG. 2). Besides, each of the reflecting parts 4 and 5 of the present embodiment has an optical property of 50 percent reflectance and 50 percent transmittance; however, it is not limited thereto and may be determined accordingly in consideration of a relative balance of light intensity between the respective images obtained through normalizing vision and magnifying vision. For example, the reflectance and the transmittance may be 40% and 60% respectively. Additionally, the reflecting part 4 may be a half mirror and the reflecting part 5 may be a total reflection mirror. In contrast, the reflecting part 4 may be the total reflection mirror and the reflecting part 5 may be the half mirror.

After the reflecting parts 4 and 5 are formed, a flat plate 2b which is formed of the same material as the flat plate 2a is joined to the flat plate 2a (See the step (b) in FIG. 2). On a rear surface (a joint surface) of the flat plate 2b, a convex part is formed to be interfitted to the reflecting part 5. For the joint of the flat plates 2a and 2b, a monomer of the material used in forming the flat plates 2a and 2b may be used as an adhesive, or an adhesive generally used for inter-resin adhesion may be used. Besides, instead of joining the flat plate 2b to the flat plate 2a, the thickness of the flat plate 2a may be increased by polymerizing and hardening the monomer formed of the same material as the flat plate 2a while being kept in contact with a front-surface side of the flat plate 2a so as to embed the reflecting part 5. It is essential for the flat plate 2b only to have such thickness that the reflecting part 5 is not cut when forming the front side refractive surface 10a of the optical part 2.

After joining the flat plates 2a and 2b, the front side refractive surface 10a is formed by cutting a front surface of the flat plate 2b so that it has the predetermined curvature (See the step (c) in FIG. 2). Thus, the optical part 2 having the predetermined refractive power may be obtained. In addition, the coating layer 6 is formed by coating the rear surface 10b with highly biocompatible resin since the reflecting part 4, as it is, is exposed on a surface of the optical part 2 (the rear surface 10b). As for a material used for forming the coating layer 6, such one that is highly biocompatible and transparent may be sufficient. For example, the coating layer 6 is formed of PMMA, polypropylene, polyimide or the like. Besides, the coating layer 6, being formed on the rear surface 10b in the present embodiment, may be formed all over the optical part 2.

After forming the optical part 2 as described above, the intraocular lens 1 is brought to completion by joining the optical part 2 and the supporting parts 3 which are formed separately. Besides, the three-piece-type intraocular lens is explained as an example in the present embodiment; however, the present invention may be applied to a one-piece-type intraocular lens where an optical part and supporting parts are formed integrally.

Next, a state of the intraocular lens having the above-described constitution, which is arranged inside the eye, is shown in FIG. 3, and a function of the intraocular lens will be explained. A light bundle (indicated by dotted lines) from an object (an object point), which is located at a predetermined short (near) distance (for example, 30 cm-50 cm) in front of the intraocular lens 1 arranged in a predetermined position inside the eye, enters the intraocular lens 1 after being refracted to some degree by the cornea. Then, a part of the light bundle which has entered and passed through the front surface 10a, enters the reflecting part 4, where a part of the incident light bundle is reflected toward the front surface 10a. Further, apart of the light bundle enters the reflecting part 5, where a part of the incident light bundle is reflected toward the rear surface 10b and passes through the rear surface 10b, so as to form the image on the retina. The above-described combination of the reflecting parts 4 and 5 forms a reflecting folded telescopic system, so that the image of the object located at the predetermined short distance in front is formed on the retina as the image under high magnification.

Incidentally, a light bundle (indicated by full lines) from an object located at an infinite distance (for example, a long (far) distance of 5 m or more) in front of the intraocular lens 1 arranged in the predetermined position inside the eye, enters the intraocular lens 1 after being refracted to some degree by the cornea. Then, the light bundle passes through the front surface 10a, the reflecting part 5, the reflecting part 4 and the rear surface 10b, so as to form the image on the retina as the image under the same magnification.

As described above, the light bundle which has been reflected by the reflecting parts 4 and 5 forms the magnified image on the retina, so that in the short distance, for example, the magnified image may be obtained (magnifying vision). Moreover, the light bundle which has passed through the reflecting parts 4 and 5 forms the image under the same magnification, so that the image under the normal magnification (the image under the same magnification as the image seen with the phakic eye) may be obtained (normalizing vision).

FIGS. 4A to 4C are examples of intraocular lenses (optical parts) which may be substituted for the intraocular lens (optical part) in FIG. 1. FIG. 4A is the example of the intraocular lens (optical part) of a meniscus shape, which has the Cassegrainian reflecting telescopic system. FIG. 4B is the example of the intraocular lens (optical part) of the biconvex shape, which has a Gregorian reflecting telescopic system. FIG. 4C is the example of the intraocular lens (optical part) of the meniscus shape, which has the Gregorian reflecting telescopic system. Besides, the shape of the optical part is not limited thereto and may be the shape of another general intraocular lens.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An intraocular lens to be arranged inside an eye comprising:
    an optical part having predetermined refractive power, which includes a front side refractive surface and a rear side refractive surface;
    a supporting part for supporting the optical part within the eye;
    a first reflecting part formed at a rear surface side of the optical part, for reflecting a part of an incident light bundle, which has passed through the front surface, toward the front surface, and transmitting a rest of the incident light bundle toward the rear surface; and
    a second reflecting part formed at a front surface side of the optical part, for transmitting a part of the incident light bundle, which has passed through the front surface, toward the rear surface, and reflecting a part of the incident light bundle, which has been reflected by the first reflecting part, toward the rear surface,
    wherein the first reflecting part and the second reflecting part are formed in a size with which the incident light bundle at an infinite distance to the optical part enters at least one of the first reflecting part and the second reflecting part,
    the intraocular lens forms a magnified image on a retina of the eye by the incident light bundle, which has passed through the front surface, has been reflected by a reflecting telescopic system constituted of the first reflecting part and the second reflecting part, and has passed through the rear surface, and
    the intraocular lens forms an image under approximately the same magnification as an image seen with a phakic eye on the retina by the incident light bundle, which has passed through the front surface, has passed through the first reflecting part and the second reflecting part, and has passed through the rear surface.

2. The intraocular lens according to claim 1, wherein the reflecting telescopic system formed by the first reflecting part and the second reflecting part includes a Cassegrainian or Gregorian reflecting telescopic system.

3. The intraocular lens according to claim 1, wherein the first reflecting part is formed to be approximately ring-shaped on a peripheral part at the rear surface side of the optical part, and the second reflecting part is formed to be approximately circular in a central part at the front surface side of the optical part.

4. The intraocular lens according to claim 1, wherein at least one of the first reflecting part and the second reflecting part is formed to be exposed on a surface of the optical part, and coated with a biocompatible material.

* * * * *